United States Patent [19]

Olstad

[11] Patent Number: 5,568,811
[45] Date of Patent: Oct. 29, 1996

[54] METHOD FOR MOTION ENCODING OF TISSUE STRUCTURES IN ULTRASONIC IMAGING

[75] Inventor: Bjørn Olstad, Ranheim, Norway

[73] Assignee: Vingmed Sound A/S, Horten, Norway

[21] Appl. No.: 372,116

[22] Filed: Jan. 13, 1995

[30] Foreign Application Priority Data

Oct. 4, 1994 [NO] Norway .................................. 943696

[51] Int. Cl.$^6$ ....................................................... A61B 8/00
[52] U.S. Cl. ......................... 128/660.07; 128/916; 73/627
[58] Field of Search ........................ 128/660.07, 660.08, 128/661.01, 661.02, 661.08, 661.09, 661.1, 916; 73/627, 861.25

[56] References Cited

U.S. PATENT DOCUMENTS

| | | | |
|---|---|---|---|
| 5,148,809 | 9/1992 | Biegeleisen-Knight et al. .. | 128/660.07 |
| 5,195,521 | 3/1993 | Melton, Jr. et al. .. | |
| 5,211,169 | 5/1993 | Freeland .............................. | 128/661.08 |

OTHER PUBLICATIONS

Drebin, R. A., et al, "Volume rendering", *Computer graphics* 22(4):65–74, Aug. 1988.

Levoy, M., "Volume rendering: Display of surfaces from volume data", *IEEE Computer Graphics and Applications*, pp. 29–37, May 1988.

Meinzer, Hans–Peter, et al., "The Heidelberg Raytracing Model", *IEEE Computer Graphics and Applications*, pp. 34–43, Nov. 1991.

Olstad, B., "Maximizing Image Variance in Rendering of Volumetric Data Sets", *Journal of Electronic Imaging*, 1:245–265, Jul. 1992, pp. 256–265.

Thune, N. and Olstad, B., "Visualizing 4–D Medical Ultrasound Data", *Proceedings IEEE Visualization '91*, San Diego, California, Oct. 1991.

Sabella, P., "A Rendering Algorithm for Visualizing 3d Scalar Fields", *Computer Graphics*, 22(4):51–55, Aug. 1988.

Aho, A. V., et al. *Compilers. Principles, Techniques and Tools*, Addison Wesley Publ. Company Inc., 1986.

Amini, A. A., et al. "Using Dynamic Programming for Solving Variational Problems in Vision", *IEEE Transaction on Pattern Analysis and Machine Intelligence*, vol. 12(9), Sep. 1990, pp. 855–866.

Olstadt, B., "Active Contours with Grammatical Descriptions" *Proc. of 6th International Conference on Image Analysis and Processing*, Como, Italy, Sep. 1991.

Sedgewick, R., "Chapter 20, Pattern Matching", *Algorithms*, Addison–Wesley, 1983, pp. 257–267.

Bjoernstad, K. et al. "Quantitative Computerized analysis of Left Ventricular Wall Motion", *Computerized Echocardiography*, S. Domenicucci ed., 1993, pp. 41–55.

Borgefors, G., "Centres of Maximal Discs in the 5–7–11 Distance Transform", *Proc. of the 8th SCIA, Tromsø*, 1993 pp. 105–111.

Borgefors, G., "Distance Transformations in Digital Images", *Computer Vision, Graphics and Image Processing* 34, 1986, pp. 344–371.

Tomtec Imaging Systems Echo–Scan operating instructions (table of contents only).

Maehle, J., et al. "Three–Dimensional Echocardiography for Quantitative Left Ventricular Wall Motion Analysis", *Echocardiography*, vol. 11, No. 4, 1994, pp. 397–408.

*Primary Examiner*—George Manuel
*Attorney, Agent, or Firm*—Rothwell, Figg, Ernst & Kurz

[57] ABSTRACT

A method for motion encoding of tissue structures in ultrasonic imaging for investigation of living bodies, comprising the steps of obtaining 2D or volumetric data sets (4) by ultrasonic measurements covering a selected region within a living body, localizing at least one tissue structure within said selected region, measuring the movement of said at least one tissue structure within said selected region by correlating said selected region between at least two instants of time, computing from said data sets with respect to said at least one tissue structure a local motion characteristic estimate, and visualizing said at least one structure as well as said motion characteristic estimate.

16 Claims, 4 Drawing Sheets

| OPERATION | NOTATION | DEFINITION |
|---|---|---|
| UNION | $L \cup M$ | $L \cup M = \{s \mid s \text{ IS ACCEPTED BY } L \text{ OR } M\}$ |
| CONCATENATION | $LM$ | $LM = \{st \mid s \text{ IS ACCEPTED BY } L \text{ AND } t \text{ IS ACCEPTED BY } M\}$ |
| KLEENE CLOSURE | $L*$ | $L* = \cup_{i=0}^{\infty} L^i$ |

FIG. 2

| STATE | CHARACTER | NEXT 1 | NEXT 2 |
|---|---|---|---|
| S0 |  | S4 | - |
| S1 | A | S2 | - |
| S2 |  | S1 | S3 |
| S3 | B | S7 | - |
| S4 |  | S2 | S5 |
| S5 | A | S6 | - |
| S6 | C | S7 | - |
| S7 | D | S8 | - |
| S8 |  | S0 | S0 |

METHOD FOR MOTION ENCODING OF TISSUE STRUCTURES IN ULTRASONIC IMAGING

BACKGROUND OF THE INVENTION

This invention relates to a method for motion encoding of tissue structures in ultrasonic imaging for the investigation of living bodies. More specifically, the invention relates to the field of ultrasound diagnosis of the cardiovascular system, particularly methods for measuring and visualizing tissue wall movement and wall structure based on time dependent 2D or volumetric ultrasound acquisition.

The terms tissue structures, tissue walls, interfaces or boundaries are used to designate more or less the same object throughout the present description.

Techniques for acquiring 2D, 3D and 4D ultrasonic studies are known as described, for example, in Tomtech Systems Inc., Echoscan User Manual, USA 1993. Visualization techniques like surface shading, depth shading, max/min rendering, average rendering, surface texturing and transparency models are also known, as described in R. A. Drebin, L. Carpenter, and P. Hanrahan, "Volume rendering" *Computer graphics*, 22(1):65, 74, August 1988; M. Levoy, "Volume rendering: Display of surfaces from volume data" *IEEE Computer Graphics and Applications*, pages 29–37, May 1988; Hans-Peter Meinzer, Kirsten Meetz, et al., "The Heidelberg raytracing model", *IEEE Computer Graphics and Applications*, pages 34–43, November 1991; Bjørn Olstad, "Maximizing image variance in rendering of columetric data sets", *Journal of Electronic Imaging*, 1:245–265, July 1992Børn Olstad and Nils Thune, "Visualizing 1-d medical ultrasound data" *Proceedings IEEE Visualization '91*, San Diego, Calif., October 1991; and P. Sabella, "A rendering algorithm for visualizing 3d scalar fields", *Computer Graphics*, 22(4):51–55, August 1988.

The invention relates to a combination of surface detection in ultrasonic imaging and transparent rendering through the usage of the distance transform. The distance transform is discussed in G. Borgefors, "Centres of maximal discs in the 5-7-11 distance transform", *Proc. of the 8th SCIA, Tromsø*, 1993; and G. Borgefors, "Distance transformations in digital images", *Computer vision, graphics and image processing* 34, 1986, pp. 344–371.

Wall motion encoding has earlier been described in multislice ultrasonic imaging Jørgen Mæle et al. "Three-Dimensional Echocardiography for quantitative left Ventricular Wall Motion Analysis: A Method for Reconstruction of Endocardial Surface and Evaluation of regional Disfunction" *Echocardiography* 1994-11,4 page 397–408; Knut Bjørnstad et al. "Quantitative Computerized Analysis of Left Ventricular Wall Motion"*Computerized Echocardiography*. Pezzano 1993, page 41–55.

SUMMARY OF THE INVENTION

The invention provides an improved visualization in 4D ultrasonic imaging that combines geometry, echogenicity properties and motion characteristics of tissue structures. The visualization of echogenicity properties differs from known methods in that the present techniques can smoothly bridge the gap between volume rendering and 2D slicing in multidimensional ultrasonic imaging. The technique can be applied both in volume rendering and as a 2D slicing technique with an intelligent and controllable opacity along the normal axis of the 2D slice plane.

The boundary detection method differs from previous imaging systems in that a global optimization framework is specified where application specific knowledge can be encoded to optimize the decision power of the boundary detection. In addition, the boundary is extracted with an optimal regression routine and will therefore not be threshold driven. This property increases the information content in the final volume rendering that displays intensity values sampled in the vicinity of the detected boundaries.

The volume rendering strategy differs from known methods in that the underlying image attributes are utilized and hence volume renderings with characteristics similar to 2D imaging are obtained. The opacity values computed as a function of the distance transform assures that the visualization emphasizes on wall structures and does not degenerate to traditional average rendering. Furthermore, the controllable opacity values depending on the distance transform can extract values from the entire wall and will give a more reliable and informative display of the walls echogenicity than a textural pattern extracted at the boundary itself as described, for example, in Tomtech Systems Inc., *Echoscan User Manual*, USA 1993. A boundary detection scheme not driven by threshold parameters further improves the information content extracted from the voxel shells in the vicinity of the boundary.

In the invention volumetric images are considered and there is no use of a global shape model before the motion analysis can be conducted. This removes the established weaknesses with the problem of correctly extracting global shape models from ultrasonic images.

Applied to 2D ultrasonic imaging the invention adds motion characteristics in an explicit manner to real time blood quantification as shown, for example, in U.S. Pat. No. 5,195,521, to M. E. Hewlett and T. A. Shoup and with respect to analysis and measurement of temporal tissue variations as described in Norwegian Patent Application No. 94.3269 filed Feb. 09, 1994.

On the background of known techniques this invention takes as a starting-point known methods for acquisition of 2D, 3D and 4D ultrasound real time blood/tissue classification in 2D imaging, arbitrary 2D slicing in multidimensional data sets, local gradient estimation and techniques for volume visualization. The invention includes new techniques for boundary detection based on global regression analysis and how a boundary structure can be utilized to obtain volume renderings of echogenicity variations in the imaged walls. The invention further includes color encoding of the local wall movement to indicate local motion characteristics, such as velocity, acceleration or phase variations, across the boundary surface.

One embodiment of the present invention includes the steps of:
- obtaining 2D or volumetric data sets by ultrasonic measurements covering a selected region in the form of a plane or volume within a living body,
- localizing at least one tissue structure within said selected plane or volume,
- measuring the movement of said at least one tissue structure within said selected plane or volume by correlating said selected plane or volume between at least two instants of time,
- computing from said data sets with respect to said at least one tissue structure (a) local velocity estimate(s) and/or (an) acceleration estimate(s) and/or (a) phase estimate(s), and
- taking the computed estimate(s) as a basis for color encoding and visualizing velocities of said at least one tissue structure.

For visualization of wall structure the invention includes a method for obtaining the tissue interfaces.

The invention includes an optimal global analysis that significantly improves the quality of boundary localization and can identify a sequence of interfaces such as for example both endocard and epicard. It also includes a framework for modeling of application specific a priori knowledge. The boundaries are not based on thresholding. This property significantly increases the potential of the subsequent volume rendering.

Based on the boundary detection described here or previously known techniques for boundary localization, the invention includes a scheme for computation of opacity values based on a binarization of the tissue boundaries and a three-dimensional distance transform. Each voxel (volume element) is labeled with:

1. The magnitude of the underlying image gradient at the closest tissue boundary.
2. A logical value that indicates whether the voxel is on the brightest side of the closest tissue boundary.
3. A three-dimensional vector that holds the offset to the closest tissue boundary. The distance to the closest boundary is then given by the magnitude of this vector.
4. The image attributes obtained in the ultrasonic acquisition and, optimally attributes computed from the information in the underlying ultrasonic acquisition.

Moreover, it is described how an opacity function for the subsequent volume rendering can be computed based on the voxel labels 1, 2, 3 and 4 referred to above. This method provides the advantages of:

1. The volume renderings get a local image signature similar to traditional two-dimensional ultrasonic imaging. The users interpretation knowledge developed for two-dimensional ultrasonic imaging is therefore easily transferred to the corresponding three- and four-dimensional modalities. Animation, depth encoding or stereo will in addition give the user a comprehension of the three-dimensional structure of the rendered scene.
2. The renderings can be continuously deformed from an arbitrary 2D slice through the volumetric data set. The method is therefore useful as a generalization of interactively positioning an arbitrary plane in a 3D or 4D data set.
3. The method is useful for analyzing the correspondence between different image attributes. The comparison can be accomplished by selecting one attribute for the opacity computations and another for the actual density values being rendered.

The invention also includes techniques for rendering of tissue boundaries with a color encoding that reflects the local velocity, acceleration or phase anomaly of the wall segment. Three methods are described in this regard:

1. Rendering of direct velocity measurements based on Doppler techniques as known per se.
2. Rendering of velocity measurements obtained by techniques for motion compensation developed in video compression and generalized to three-dimensional imaging. The velocities are obtained as the motion estimates and opacity values are assigned as a function of the local correlation function. The opacity function can in this way be utilized to reduce the effect of unreliable motion estimates in the final rendering.
3. The values of the distance transform in adjacent volumes at the position of a detected boundary are used to obtain velocity, acceleration and phase anomaly estimates.

The method of the present invention provides the additional advantages of:

1. Wall motion abnormalities, such as the movement of endocard in the left ventricle, can be displayed as a color encoding of a surface and is therefore more easily interpreted.
2. The technique can be efficiently implemented and will render values detected in the image scene in contradiction to prior art based on modeling and detection of for example the entire left ventricle geometry. Such object recognition algorithms must fill in image dropouts and generate surface patches even in situations where there is no evidence in the underlying ultrasonic images. Previously known techniques are therefore presenting information from a model and not directly from the actual measurements. It is also generally recognized that the task of automatic object recognition in ultrasonic imaging includes a high risk for both local and global errors.

The wall motion encoding described in this specification also applies to 2D ultrasonic imaging. In this case the invention adds motion characteristics in an explicit manner to any real time tissue interface localization including the real time blood quantification as discussed in U.S. Patent No. 5,195,521, issued Mar. 23, 1993 and with respect to analysis and measurement of temporal tissue variations as described in Norwegian Patent Application No. 94.3269 filed Feb. 09, 1994.

In view of the above background and explanations, the following are important aspects of this invention:

1. A global regression framework that models a priori knowledge is utilized for boundary detection. This technique significantly improves the boundary localization in situations with a poor signal to noise ratio and is not threshold driven.
2. A controllable localization of the volume rendering to the vicinity of tissue boundaries is specified through the opacity definition. This approach is useful for both generalized 2D slicing with depth information and complete volume rendering of multidimensional ultrasonic images.
3. The visualization of wall segments extracted from volumetric ultrasonic studies are color coded to indicate velocity, acceleration and phase variations. The method relates directly to the measured data and is not dependent on a model and associated object recognition routine. This approach significantly improves the reliability of the technique.

These aspects as well as other novel and specific features according to this invention, are intended to be covered by the claims.

BRIEF DESCRIPTION OF THE DRAWINGS

The invention shall be explained more closely in the following description with reference to the drawings, in which.

DETAILED DESCRIPTION OF THE PREFERRED EMBODIMENTS

Detection of Tissue Interfaces

The quality of the localization of tissue interfaces in ultrasonic images is of fundamental importance both in the quantitative evaluation of volumes/areas and for volume visualizations that emphasize the geometry or internal structure of tissue boundaries.

Figure 1:
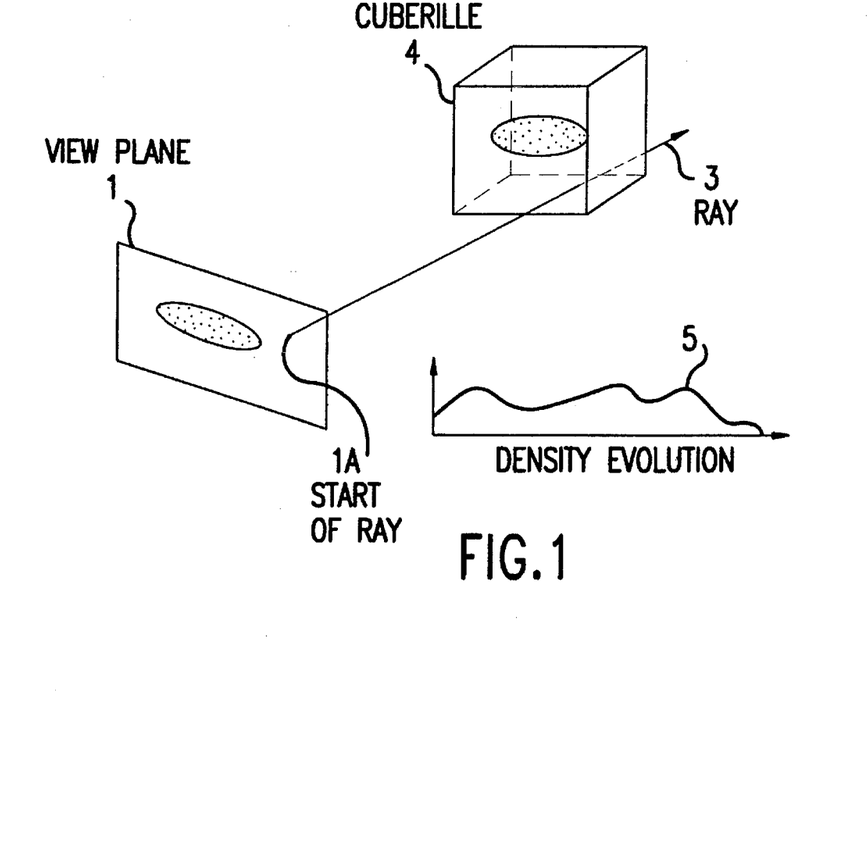
FIG. 1 gives a highly schematic framework for the rendering process.

FIG. 1 illustrates the rendering process usually employed in the prior art. A point 1A in the view plane 1 is associated with a line 3 in 3D through the perspective mapping. A density evolution can be defined by extracting interpolated values from the volumetric data set or cuberille 4 along the ray 3. For rendering of wall structures it is necessary to identify the position where the ray 3 enters into the wall, for example the position where the ray goes from blood to tissue. The invention includes a global regression framework that can be used to estimate the position of one or a number of tissue interfaces. The estimation results for each ray can be integrated to a complete set of surfaces by using known techniques for 2D image processing, regarding the view plane 1 as an image with the transition candidates for each ray 3 as image elements.

Assume for example, that an ideal signal f(t) has been degraded by a noise process n(t) to produce the distorted, observed signal g(t)=f(t)+n(t). g(t) denotes the density evolution extracted along a line intersecting the volumetric data set. Known techniques for the estimation of f(t) include the maximum likelihood estimator for f(t) based on a statistical model of the noise process n(t). This type of approach only exploits a priori information about the noise process. In ultrasonic imaging of the cardiovascular system there is also a priori knowledge available about the structural properties possessed by f(t). In imaging of the left ventricle one might, for example, assume that f(t) includes a number of samples from blood, followed by the endocard transition, followed by a number of samples from myocard, followed by the epicard transition and then followed by a number of tissue samples. The invention utilizes a signal model with a number of transitions that can be used for a nonlinear regression. A grammatical framework is used to model a priori knowledge about f(t). Inside the grammatical framework we embed an adaptive nonlinear signal regression procedure that also can utilize knowledge about the noise process. The adaptive character is due to the possibility of adjusting the noise model to the current classification in the parsing of the grammatical model. The optimal regression result can be used to estimate f(t), but equally important a robust detection of a single or multiple tissue interfaces is obtained.

Figure 2:
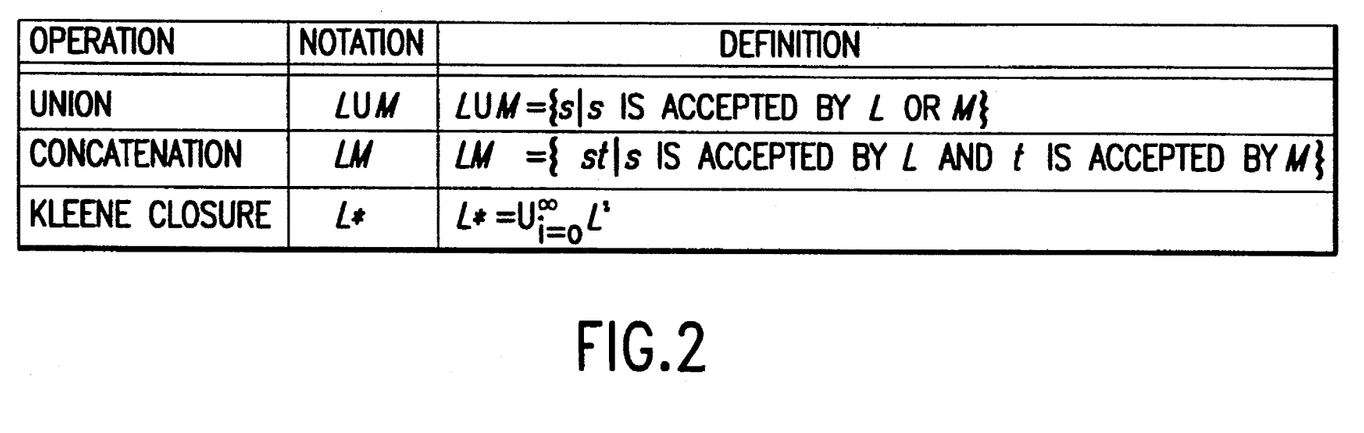
FIG. 2 gives definitions of the three basic operations for construction of regular expressions.

A grammar G, is usually specified as a set (N,Σ,P,S) where N is a finite set of nonterminals, Σ a finite set of terminals, P a finite set of productions and S the starting symbol of the grammar. See, for example, the discussion in A. V. Aho, R. Sethi and J. D. Ullman, Compilers. Principles, Techniques and Tools. Addison Wesley Publ. Company Inc., 1986. The grammar G=(N,Σ,P,S) generates a language L(G) which is the set of all strings that can be produced by G. An example of such languages is given the languages described as regular expressions. The rules that define the regular expressions over an alphabet Σ are shown in the table of FIG. 2.

Figure 3:
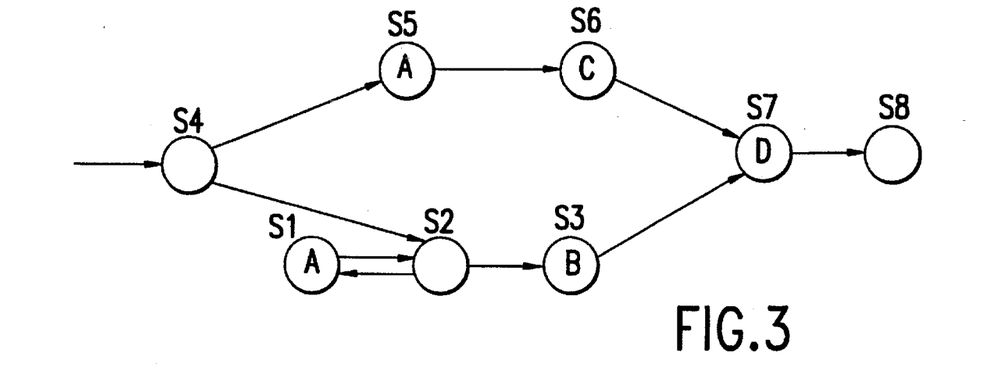
FIG. 3 is a diagram showing an example of a possible nondeterministic finite-state machine to search for the pattern description.
Figure 4:
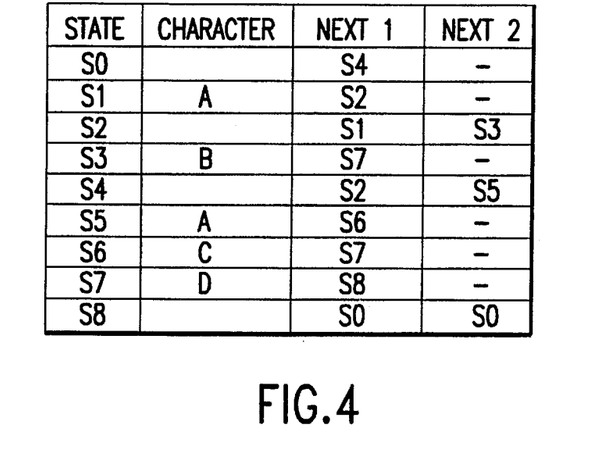
FIG. 4 illustrates a state table corresponding to the example given in FIG. 3.

In R. Sedgewick, *Algorithms*, Addison Wesley Publ. Company Inc., 1983, Sedgewick explains how the Knuth-Morris-Pratt algorithm is used for regular expression pattern matching. Because of the union operator, the algorithm must handle nondeterminism. Let us look at an example:

FIG. 3 shows one possible nondeterministic finite-state machine that could be used to search for the pattern description (A*B∪AC)D. The circles correspond to states. State S2, S4 and S8 are nonterminals; and S1, S3, S5, S6 and S7 are terminals. State S2 and S4 make this a nondeterministic machine, because from these there are two possible next states. To represent this nondeterministic machine we use a table of states. For each state we need to store the character (terminal) if it is a terminal state, and we need maximum two indices to the possible next states. The table of FIG. 4 shows the corresponding table for the above example (FIG. 3). The table can be interpreted as "If you are in State and you see Character then scan the character and go to state Next1 (or Next2)".

The invention includes two methods (M1, M2) for the embedding of nonlinear regression techniques in a structural framework:

(M1) Precomputation of nonlinear signal regressions

Let |Σ| denote the number of elements in Σ and let the input data be given by g(0), . . . , g(n−1). Compute the cost array C[i, j, k] where $0 \leq i \leq j < n$ and k=1, . . . , |Σ|. C[i, j, k] denotes the minimal error between g(i), . . . , g(j) and a nonlinear regression from a function family associated with the label k∈Σ. A parsing algorithm is then devised in order to minimize:

$$\sum_{q=0}^{Q-1} C[i_q, i_{q+1}-1, k_q] \quad (1)$$

when $i_0=P<i_1<i_2< \ldots <i_Q=n$ and $k_o \ldots k_o k_1 \ldots k_1 \ldots k_{Q-1}$ belongs to the language of G. (The symbol $k_q$ is repeated $i_q + i - i_q$ times). The language G can also include information on absolute or relative dimensions which will translate into the number of symbol repetitions. The symbol transitions in the optimal parsing is utilized to define the localization of tissue interfaces. Hard and soft constraints are easily incorporated in the model and can be utilized to achieve continuity between neighboring rays by a 2D algorithm operating in the view plane.

(M2) Integrated computation of regressions with time-delayed discrete dynamic programming The second algorithm is similar to the contour detection algorithm proposed in B Olstad, "Active contours with grammatical descriptions", *Proc. of 6th International Conference on Image Analysis and Processing*, Como, Italy, September 1991 for object recognition, but relies on a regression framework that easily allows for the computation of C[i, j+1, k] when C[i, j, k] is known. One possibility is to use a framework for the computation of C[i, j, k] similar to the time-delayed discrete dynamic programming algorithm utilized in the active contour algorithm for boundary detection described in A. A. Amini, T. E. Weymouth and R. C. Jain, "Using dynamic programming for solving variational problems in vision" *IEEE Transaction on Pattern Analysis and Machine Intelligence*, vol. 12(9), September 1990. If the number of legal values are limited to M, one can construct a state space with M elements for the dynamic programming algorithm: f(i)=0,f(i)=1, . . . , f(i)=M−1. Similarly to the active contour algorithm, more elaborate regression measures might require that the state space is increased to $M^2$ elements considering all possible pairs of adjacent f-values.

In both cases, significant algorithmic improvements are obtained with heuristic approaches to the optimization problem such as repeated binary subdivision of intervals.

Visualization of echogenicity in wall structures.

This aspect of the present method assumes that the volumetric data set has been converted to a binary volume either by the boundary detection method according to this invention or prior techniques for boundary detection. Of particular interest is the edge detection reported in E. Steen and B. Olstad, "Volume rendering in medical ultrasound imaging", *Proceedings of 8th Scandinavian Conference on Image Analysis*, Tromsø, Norway May 1993 where also the level of detail can be easily regulated.

Figure 5:
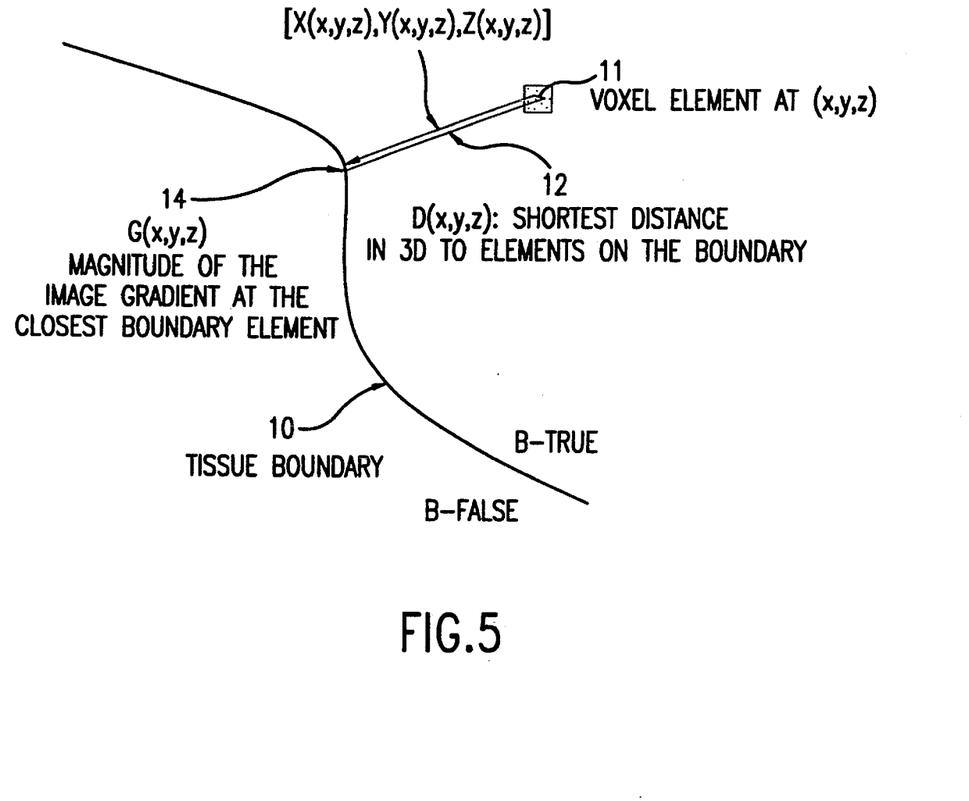
FIG. 5 illustrates voxel encodings according to the invention for definition of the opacity function.

In FIG. 5 there is shown a tissue boundary 10 and a voxel element 11 at (x,y,z). FIG. 5 illustrates how the binary volume has been utilized to obtain an encoding of each voxel for definition of the opacity function. All values can be efficiently computed by a three-dimensional distance transform as is described in G. Borgefors, "Centres of maximal discs in the 5–7–11 distance transform" *Proc. of the 8th SCIA, Tromsø*, 1993. In addition to the original image attributes, each voxel is labeled with:

D(x,y,z): Distance 12 to closest boundary in 3D.

[X(x,y,z),Y(x,y,z),Z(x,y,z)]: Computed such that (x+X,y+Y,z+Z) is the position of the closest boundary.

G(x,y,z): Magnitude of image gradient at the closest boundary, as indicated with 14 in FIG. 5.

B(x,y,z): A logical value equal to TRUE if the voxel is at the brightest side of the closest boundary.

B(x,y,z) is to used to select a specific side of a boundary such as samples from myocard instead of blood samples in the vicinity of endocard. If the boundary detection method described here is utilized, one can use the classification obtained by the symbol encoding to for example reject all pixels outside myocard. Rejected voxels are assigned an opacity value such that they become completely transparent. Nonrejected voxels are assigned an opacity value by mapping D(x,y,z) through a nonlinear, monotone function such as the exponential function. G(x,y,z) might be utilized as a scaling factor in the opacity definition in order to for example emphasize on significant transitions in the data set. Finally, the original image attributes are rendered with for example the technique described in E. Steen and B. Olstad, "Volume rendering in medical ultrasound imaging", *Proceedings of 8th Scandinavian Conference on Image Analysis*, Tromsø, Norway May 1993 utilizing the opacity values described here.

The final renderings provide information about the structural echogenicity variations in a layer behind a tissue interface or in a layer between two interfaces such as the layer between endocard and epicard. In 3D and 4D imaging with contrast agents for ultrasonic imaging the invention comprises a framework for mapping perfusion variations in myocard.

Figure 6:
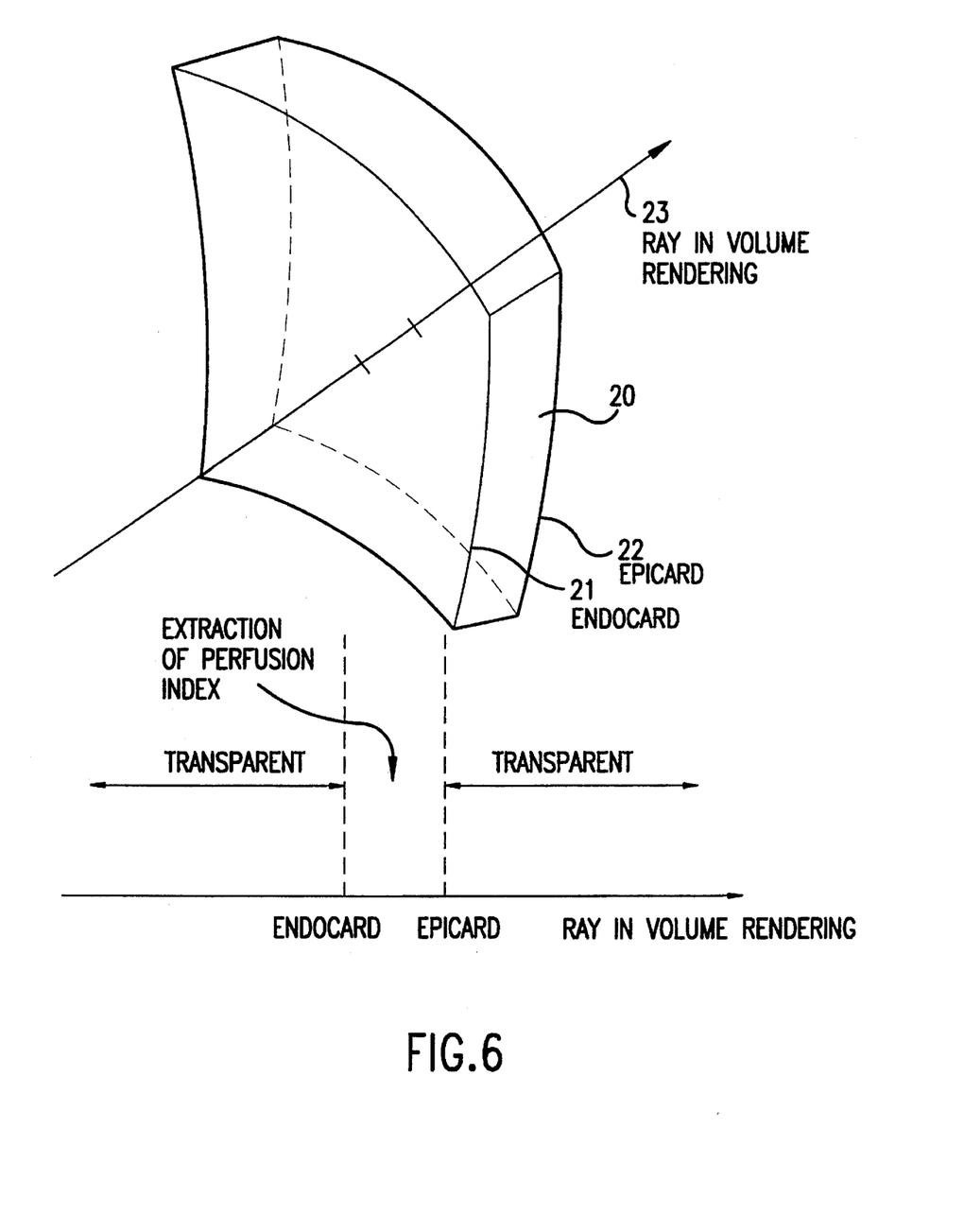
FIG. 6 gives a schematic framework for rendering of perfusion variations in myocard which is useful for 3D and 4D ultrasonic imaging with contrast agents.

FIG. 6 illustrates this rendering of perfusion variations in myocard 20, whereby a small segment of myocard is shown, and the processing for one of the rays 23 in the volume rendering. At 21 and 22 the endocard and the epicard respectively are indicated.

Encoding of wall movements

This essential aspect of the present method assumes that a sequence of volumetric data sets (cuberille 4 in FIG. 1) is available and that the time difference between the acquisitions of each volume is known. A typical situation might be data acquired by ECG-triggering where a specific volume is acquired at a fixed delay after the ECG pulse or real-time imaging where complete volumes are acquired with a sufficiently high framerate.

Let (x,y,z) denote a voxel located on a tissue boundary. The most important example is probably endocard in ultrasonic studies of the left ventricle function. The invention provides for a color encoding of the boundary elements that reflects properties of the wall motion. Examples are velocity encoding, acceleration encoding and phase anomaly encoding. Velocity encoding can be obtained as a function of D(x,y,z) where D is the value of the distance transform at the corresponding voxel in the adjacent data volumes. Knowing D(x,y,z) in both adjacent volumes, one can also estimate acceleration and a phase indicator. The accuracy of these estimates increases with the number of available consecutive wall positions. The wall motion indicators are displayed as a color encoding of the surface defined by the tissue boundary or as a color encoding in combination with other volume rendering techniques.

Knowing all three components of the local velocity vector [X,Y,Z] it is also possible to compensate for global movement of the heart during the ECG cycle.

The motion encoding can be utilized with other velocity estimations as well:

1. If direct velocity estimates are obtained with the ultrasonic imaging through measurements of Doppler shifts, the velocity estimates can be rendered with the technique described here for visualization of echogenicity in wall structures or a maximum rendering can be utilized for voxels inside a given limit value for the opacity function.

2. Known techniques for motion compensation in compression of video sequences include reliable techniques for locating an image region in the adjacent video frame. These techniques can be generalized to 3D by searching for a small data cube in the previous data volume. The techniques produce local estimates for the velocity vectors. In addition, the correlation coefficient between the small data cube and the optimal subcube in the previous data volume can be utilized to define an opacity function. Estimates with low correlation coefficients are made transparent such that the uncertain estimates only mildly influence the final velocity encoding.

As already mentioned above the wall motion encoding described in this specification also applies to 2D ultrasonic imaging. In this case the invention adds motion characteristics in an explicit manner to any real time tissue interface localization including the real time blood quantification like that described in U.S. Pat. No. 5,195,521, and with respect to analysis and measurement of temporal tissue variations as described in Norwegian Patent Application No. 94.3269 filed Feb. 09, 1994. The technical solutions are completely analogous to the 3D situation. All computations are restricted to a 2D plane. This includes the distance transform referred to and the encoding of the velocity components.

As a short summary of the above description, this invention comprise a method for measurement and visualization of wall movement and wall structure based on ultrasonic 3D and 4D acquisitions. The method can be used for investigation of living biological structures, in particular during movement, for example a heart function. The main application will be in hospitals and the like. The method is based on a single or a sequence of volumetric data sets obtained with ultrasonic imaging. The methodology may be applied to prerecorded data or a sequence of volumetric data sets obtained with realtime 3D ultrasonic imaging. Each volumetric data set is first analyzed and tissue boundaries or blood/tissue boundaries are localized with a scale-space technique that can vary the local level of detail. The detected boundaries are converted to a binary volume which is coded with the distance transform that labels the entire volume with the minimal distance to the detected boundaries. The wall structure is then visualized by utilizing the computed distance map and the direction of the intensity gradient as input to the opacity computation. Any image modality for ultrasonic imaging, including amplitude imaging, can then be rendered by projecting the volume elements to the view plane with the opacity values according to this invention. Secondly, the distance map is utilized as a color encoding on the tissue boundaries in the adjacent data sets if a sequence of volumetric data sets is available. The invention also includes a method for velocity estimation for motion compensation in image sequences to three-dimensional imaging combined with opacity computations that reflects the significance of the velocity estimate. In both cases the information includes a full 3D vector describing the wall movement of a small segment of the tissue boundary. The velocity encoding can compensate for global motion of for example the heart by subtracting a global motion estimate from the local velocity estimates. Derived information such as acceleration or the phase of the movement can also be computed and projected to the view plane. Finally, the structural encoding and the velocity encoding of the wall are combined in the rendered views.

I claim:

1. A method for motion encoding of structures in ultrasonic imaging comprising the steps of:
   obtaining data sets by ultrasonic measurements covering a selected region within a body;
   localizing at least one structure within said selected region, from said data sets;
   measuring the movement of said at least one structure within said selected region by correlating said at least one structure between at least two instants of time, thereby providing at least one correlated structure;
   computing from said data sets, with respect to said at least one correlated structure a local motion characteristic estimate including local spatial displacement defining local velocity, local acceleration, and local phase; and
   visualizing said at least one structure as well as said motion characteristic estimate.

2. The method according to claim 1, further comprising the step of computing distance transform with respect to said selected region considered on at least two instants of time, and using the resulting correlation as temporal tracking of each point on the tissue structure boundaries for said computing of said motion characteristic estimate.

3. The method according to claim 1, further comprising the step of using 3D motion compensation techniques to obtain said local motion characteristic estimates for volume rendering.

4. The method according to claim 3, further comprising the step of using the correlation function of the motion compensation to define an opacity function in the volume rendering in order to reduce the dependence on unreliable motion estimates.

5. The method according to claim 4, whereby visualization of perfusion variations in myocard is provided for by
   administering an ultrasound contrast agent to said myocard,
   defining said opacity function such that echogenicity values outside myocard become transparent, and
   using said opacity function to visualize echogenicity values.

6. The method according to claim 1, further comprising the visualization of direct motion characteristic estimates of said structures by measurements of Doppler shift caused by movement of the tissue structures.

7. A method according to claim 1, further including the step of computing an opacity function as a nonlinear, monotone mapping of the distance to the closest point of said tissue structure to visualize echogenicity values in at least one of said structures.

8. A method according to claim 1, whereby said localizing of at least one structure is provided for by a global regression routine with a sequence of local regressions, and interfaces in said tissue structure are defined as the optimal localization for transitions between the local regressions.

9. A method for motion encoding of structures in ultrasonic imaging comprising the steps of:
   obtaining data sets by ultrasonic measurements covering a selected region within a body;
   localizing at least one structure within said selected region;
   measuring the movement of said at least one structure within said selected region by correlating said selected region between at least two instants of time;
   computing from said data sets, with respect to said at least one structure a local motion characteristic estimate;
   visualizing said at least one structure as well as said motion characteristic estimate; and
   computing an opacity function as a nonlinear, monotone mapping of the distance to the closest point of said tissue structure to visualize echogenicity values in at least one of said structures.

10. The method according to claim 7, whereby said visualization of motion characteristics and said visualization of echogenicity derived therefrom, is provided for simultaneously on at least two separate displays or screen windows.

11. A method according to claim 7, whereby said visualization of motion characteristics and said visualization of echogenicity or signal characteristics derived therefrom, is provided for in a common display or screen window by encoding in the color space.

12. The method according to claim 7, further comprising the step of computing the distance to the closest point of said structure with a three dimensional (3D) distance transform.

13. The method according to claim 8, further comprising the steps of using the distance along the ray utilized in the volume rendering as an approximation of the true minimal distance in 3D in order to increase the speed of the volume rendering.

14. A method for motion encoding of structures in ultrasonic imaging comprising the steps of:
   obtaining data sets by ultrasonic measurements covering a selected region within a body;
   localizing at least one structure within said selected region, from said data sets, provided for by a global regression routine with a sequence of local regressions, and interfaces in said tissue structure are defined as the optimal localization for transitions between the local regressions;
   measuring the movement of said at least one structure within said selected region by correlating said at least one structure between at least two instants of time, thereby providing at least one correlated structure;
   computing from said data sets, with respect to said at least one correlated structure a local motion characteristic estimate; and visualizing said at least one structure as well as said motion characteristic estimate.

15. A method according to claim 8, further comprising the step of utilizing symbol encodings representing local interpretations of the local characteristics that are obtained in the optimal regression for selection of tissue segments in volume rendering.

16. A method according to claim 8, further comprising the step of algorithmically obtaining the optimal regression by precomputation of nonlinear signal regressions, and integrated computation of regressions with time-delayed discrete dynamic programming.

* * * * *